US012612355B2

(12) United States Patent (10) Patent No.: US 12,612,355 B2

Herbrecht et al. (45) Date of Patent: Apr. 28, 2026

(54) PROCESS FOR THE CONTINUOUS PREPARATION OF (METH)ACRYLATE BY REACTING AN ALCOHOL WITH (METH)ACRYLIC ACID USING AT LEST ONE CONTROL UNIT WHICH IS CLOSED-LOOP CONTROLLED BY A SENSOR (S)

(71) Applicant: BASF SE, Ludwigshafen am Rhein (DE)

(72) Inventors: Dominik Herbrecht, Ludwigshafen am Rhein (DE); Cornelis Hendricus De Ruiter, Ludwigshafen am Rhein (DE); Marvin Kramp, Ludwigshafen am Rhein (DE); Maike Feuerstein, Ludwigshafen am Rhein (DE); Piotr Makarczyk, Ludwigshafen am Rhein (DE); Tile Gieshoff, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 513 days.

(21) Appl. No.: 18/039,986

(22) PCT Filed: Dec. 8, 2021

(86) PCT No.: PCT/EP2021/084768

§ 371 (c)(1),
(2) Date: Jun. 2, 2023

(87) PCT Pub. No.: WO2022/122814

PCT Pub. Date: Jun. 16, 2022

(65) Prior Publication Data

US 2024/0010603 A1 Jan. 11, 2024

(30) Foreign Application Priority Data

Dec. 11, 2020 (EP) ..................................... 20213506

(51) Int. Cl.
*C07C 67/08* (2006.01)
*G01N 21/359* (2014.01)

(52) U.S. Cl.
CPC ............ *C07C 67/08* (2013.01); *G01N 21/359* (2013.01)

(58) Field of Classification Search
CPC ................................ C07C 67/08; G01N 21/31
See application file for complete search history.

(56) References Cited

U.S. PATENT DOCUMENTS 4,280,010 A 7/1981 Erpenbach et al.
2006/0019401 A1* 1/2006 Fies ........................ C07C 67/08
436/129

FOREIGN PATENT DOCUMENTS

JP 2009062289 A * 3/2009 ............. C07C 51/84

OTHER PUBLICATIONS

International Search Report and Written Opinion received for PCT Patent Application No. PCT/EP2021/084768, mailed on Mar. 3, 2022, 9 pages.

* cited by examiner

*Primary Examiner* — Yate' K Cutliff
(74) *Attorney, Agent, or Firm* — Faegre Drinker Biddle & Reath LLP

(57) ABSTRACT

The present invention relates to a process for the continuous preparation of (meth)acrylate by reacting an alcohol with a (meth)acrylic acid using at least one control unit which is closed-loop controlled by a sensor (S).

14 Claims, 2 Drawing Sheets

PROCESS FOR THE CONTINUOUS PREPARATION OF (METH)ACRYLATE BY REACTING AN ALCOHOL WITH (METH)ACRYLIC ACID USING AT LEST ONE CONTROL UNIT WHICH IS CLOSED-LOOP CONTROLLED BY A SENSOR (S)

CROSS-REFERENCE TO RELATED APPLICATIONS

This application is a National stage application (under 35 U.S.C. § 371) of PCT/EP2021/084768, filed Dec. 8, 2021, which claims benefit of European Application No. 20213506.7, filed Dec. 11, 2020, both of which are incorporated herein by reference in their entirety.

The present invention relates to a process for the continuous preparation of (meth)acrylate by reacting an alcohol with (meth)acrylic acid using at least one control unit which is closed-loop controlled by a sensor (S).

Figure 1:
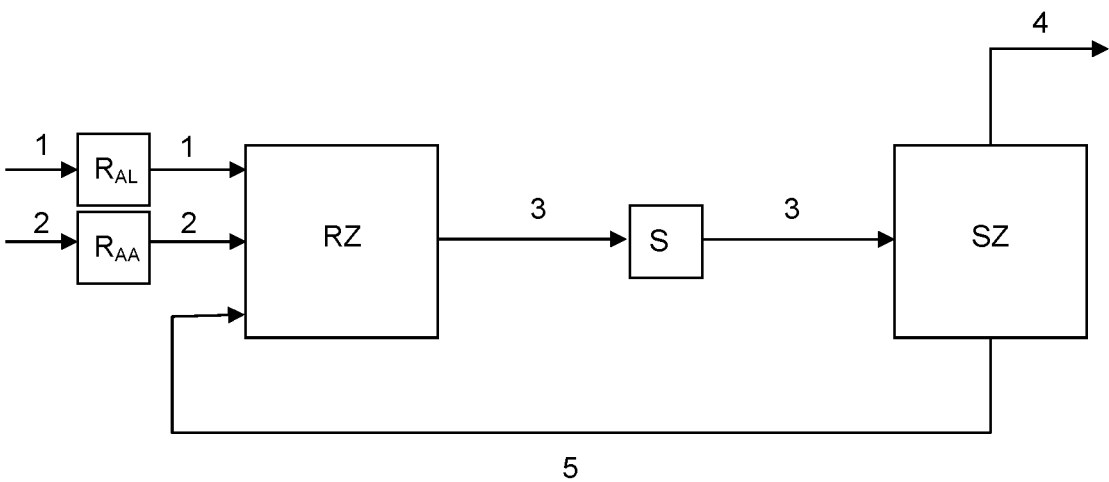
FIG. 1 is a flow diagram for one process in accordance with the present disclosure.

Polymers or copolymers prepared on the basis of (meth)acrylates are of considerable commercial importance, generally in the form of polymer dispersions, for example as adhesives, surface coatings or textile, leather and paper assistants. For applications, in particular in the food or cosmetics sector, the polymer dispersions should be substantially free of volatile impurities.

The preparation of lower (meth)acrylates by esterification of (meth)acrylic acid with lower alcohols in the presence of strong acids is generally known. The (meth)acrylic acid used is as a rule pure or prepurified (meth)acrylic acid, cf. for example Chem Systems, Acrylic Acid/Acrylates 96/97-8, November 1997, page 24.

Since the formation of the ester from (meth)acrylic acid, the (meth)acrylate, and alcohol is known to be based on an equilibrium reaction, as a rule one feedstock is used in excess and/or the resulting water of esterification and/or the desired (meth)acrylate are removed from the equilibrium in order to obtain economical conversions. The influencing of the esterification equilibrium by the use of an excess of alcohol is however disadvantageous since, inter alia, this promotes the formation of ethers from the starting alcohols and of Michael adducts (cf. for example U.S. Pat. No. 4,280,010, column 1).

To minimize the formation of Michael adducts the esterification is often carried in an essentially equimolar ratio of alcohol and (meth)acrylic acid.

If the preparation of (meth)acrylate is carried out with an essentially equimolar ratio of alcohol and (meth)acrylic acid in a reactor, fluctuations in the molar ratio of alcohol and (meth)acrylic acid lead to a decrease of the (meth)acrylate output.

In the processes in the state of the art it is difficult to control the molar ratio of alcohol and (meth)acrylic acid in the reactor and to react to fluctuations in a timely manner.

It is, therefore, an object of the present invention to provide a simple and economical process for the preparation of (meth)acrylates, in which it is possible to control the feed of alcohol and (meth)acrylic acid to the reaction zone (RZ) in a in a timely manner, which is technically simple and gives a high yield and highly pure products and in which little waste and very little polymer result.

This object is achieved by a process for the continuous preparation of a (meth)acrylate by reacting an alcohol with (meth)acrylic acid comprising the steps i) feeding a first stream (1) containing the alcohol and a second stream (2) containing the (meth)acrylic acid to a reaction zone (RZ), wherein the feed to the reaction zone (RZ) via the first stream (1) is adjusted by a first control unit ($R_{AL}$) which is closed-loop controlled by a sensor (S) and/or the feed to the reaction zone (RZ) via the second stream (2) is adjusted by a second control unit ($R_{AA}$) which is closed-loop controlled by the sensor (S), and reacting the alcohol and the (meth)acrylic acid in the reaction zone (RZ) to obtain a product mixture comprising the (meth)acrylate and unreacted (meth)acrylic acid and unreacted alcohol, ii) feeding the product mixture as a third stream (3) from the reaction zone (RZ) to a separation zone (SZ), wherein the sensor (S) determines the molar ratio of the unreacted (meth)acrylic acid and the unreacted alcohol contained in the product mixture and, wherein the sensor (S), depending on the determined molar ratio of the unreacted (meth)acrylic acid and the unreacted alcohol in the product mixture, controls the first control unit ($R_{AL}$) and/or the second control unit ($R_{AA}$), iii) separating the product mixture in the separation zone (SZ) to obtain the (meth)acrylate which is discharged from the separation zone (SZ) as a fourth stream (4) and a recycling mixture comprising the unreacted (meth)acrylic acid and the unreacted alcohol which is discharged from the separation zone (SZ) as a fifth stream (5).

It has surprisingly been found that the process according to the invention makes it possible to control the molar ratio of alcohol and (meth)acrylic acid in the total feed to the reaction zone (RZ). This is achieved by determining the molar ratio of unreacted (meth)acrylic acid and unreacted alcohol contained in a product mixture which is controls a first control unit ($R_{AL}$) which adjusts the feed of alcohol to the reaction zone (RZ) via a first stream (1) and/or closed-loop controls a second control unit ($R_{AA}$) which adjusts the feed of (meth)acrylic acid to the reaction zone (RZ) via a second stream (2).

Since in a preferred embodiment of the present invention, the determination of the molar ratio of unreacted (meth)acrylic acid and unreacted alcohol contained in a product mixture which is obtained in the reaction zone (RZ) is carried out online or inline, the process according to the invention can be carried out particularly quickly and cheaply since no sampling from the product mixture and/or third stream (3), is necessary. Since no sampling is necessary, the process according to the invention is also particularly safe. Workers do not come into direct contact with the product mixture as a result of the process according to the invention. In addition, the process according to the invention can be automated very readily, which likewise improves the economics of the process according to the invention.

Even if the determination of the molar ratio of unreacted (meth)acrylic acid and unreacted alcohol contained in a product mixture which is obtained in the reaction zone (RZ) is carried out offline, the determination by means of NIR is significantly quicker than the usual wet-chemical methods of determination.

In addition, one, two or all feed streams to the reaction zone (RZ) can be closed-loop controlled in the process for preparing (meth)acrylate by means of the molar ratio of unreacted (meth)acrylic acid and unreacted alcohol contained in a product mixture measured by the sensor (S).

Since, in a preferred embodiment of the invention, the sensor (S) determines the molar ratio of unreacted (meth) acrylic acid and unreacted alcohol contained in a product mixture by using an NIR spectrometer (by NIR spectroscopy) no additional complex measuring instuments are required in the process according to the invention, which likewise makes the process according to the invention economical.

The method according to the invention will be described in more detail below.

The novel process can be used for the preparation of both methacrylates and acrylates, preferably for the preparation of acrylates. For the purpose of the present invention the term "(meth)acrylic acid" subsumes methacrylic acid and acrylic acid. For the purpose of the present invention, moreover, the term "(meth)acrylate" subsumes methacrylate and acrylate.

Alcohol

Suitable starting materials are practically all known alcohols. The alcohols may be straight-chain, branched or cyclic. Moreover, the alcohols can carry substituents which exhibit inert behavior under the reaction conditions, for example alkoxy, alkenyloxy, alkylamino, dialkylamino and halogens (F, Cl, Br, I). According to the invention, besides monoalcohols, also diols, triols and polyols may be used.

In a preferred embodiment mono alcohols are used as alcohol. Mono alcohols have one hydroxyl group (—OH).

Suitable alcohols are, for example, those of the general formula (I):

$$R^a\text{—OH} \qquad (1),$$

wherein $R^a$ is selected from the group consisting of unsubstituted or at least monosubstituted $C_1$-$C_{30}$-alkyl, $C_3$-$C_{10}$-cycloalkyl, $C_3$-$C_{10}$-heterocyclyl comprising at least one heteroatom selected from N, O and S, $C_5$-$C_{14}$-aryl and $C_5$-$C_{14}$-heteroaryl comprising at least one heteroatom selected from N, O and S, where the substituents are selected from the group consisting of F, Cl, Br, $OR^b$, CN, $C_1$-$C_{10}$-alkyl, $C_3$-$C_{10}$-cycloalkyl, $C_3$-$C_{10}$-heterocyclyl comprising at least one heteroatom selected from N, O and S, $C_5$ $C_{14}$-aryl and $C_5$-$C_{14}$-heteroaryl comprising at least one heteroatom selected from N, O and S, where $R^b$ is selected from $C_1$-$C_{10}$-alkyl and $C_5$-$C_{10}$-aryl.

Preferred alcohols are those of the general formula (I), wherein $R^a$ is selected from the group consisting of, unsubstituted or at least monosubstituted $C_1$-$C_{30}$-alkyl, where the substituents are selected from the group consisting of $OR^b$, $C_1$-$C_{10}$-alkyl, where $R^b$ is selected from $C_1$-$C_{10}$-alkyl.

More preferred alcohols are those of the general formula (I), wherein $R^a$ is selected from the group consisting of, unsubstituted or at least monosubstituted $C_1$-$C_{10}$-alkyl, where the substituents are selected from the group consisting of $C_1$-$C_{10}$-alkyl.

Even more preferred the alcohol is selected from the group consisting of methanol, ethanol, n-propanol, n-butanol, sec-butanol, iso-butanol, tert-butanol, n-pentanol, n-hexanol, n-heptanol, n-octanol, n-nonanol, 2-ethylhexanol, tridecanol, stearyl alcohol, palmityl alcohol, benzyl alcohol, 2-phenylethanol, 2-(p-methoxyphenyl)ethanol, 2-(3,4-dimethoxyphenyl)ethanol, allyl alcohol, propargyl alcohol, 2-hydroxymethyl-furan, lactic acid and serine.

Especially preferred the alcohol is selected from the group consisting methanol, ethanol, n-propanol, isopropanol, n-butanol, isobutanol and 2-ethylhexanol. Methanol, ethanol, n-butanol, isobutanol and 2-ethylhexanol are particularly preferred.

In the process according to the invention a first stream (1) containing the alcohol is fed to the reaction zone (RZ). The first stream (1) may contain one alcohol or a mixture of two or more alcohols. Preferably the first stream (1) contains one alcohol. The first stream (1) preferably contains at least 90%—by weight of the alcohol, more preferably at least 95%—by weight of the alcohol and particularly preferred at least 97%—by weight of the alcohol, in each case based on the total weight of the first stream (1) fed to the reaction zone (RZ).

The alcohol may be fed to the reaction zone (RZ) as a liquid and/or gas.

(Meth)Acrylic Acid

In the process according to the invention a second stream (2) containing the (meth)acrylic acid is fed to the reaction zone (RZ). Preferably the second stream (2) contains acrylic acid. The second stream (2) preferably contains at least 90%—by weight of (meth)acrylic acid, more preferably at least 95%—by weight of (meth)acrylic acid and particularly preferred at least 99%—by weight of (meth)acrylic acid, in each case based on the total weight of the second stream (2) fed to the reaction zone (RZ).

In the process according to the invention crude acrylic acid or pure acrylic acid may be used.

The crude acrylic acid which in one embodiment can be used in the inventive process may contain, for example, the following components:

acetic acid 0.05 to 3% by weight, propionic acid 0.01 to 1% by weight, diacrylic acid 0.01 to 5% by weight, water 0.05 to 10% by weight, furfural 0.01 to 0.1% by weight, benzaldehyde 0.01 to 0.05% by weight, other aldehydes 0.01 to 0.3% by weight, other carbonyl-containing inhibitors 0.01. to 0.1% by weight, and maleic acid (anhydride) 0.001 to 0.5% by weight, wherein the percent-by-weight values are in each case based on the total weight of the crude acrylic acid.

In another, preferred, embodiment, pure acrylic acid is used in the process according to the invention. In other words, in a preferred embodiment, the second stream (2) consists of pure acrylic acid. The term "pure acrylic acid" for the purpose of the present invention means that the pure acrylic acid contains at least 99.5% by weight of acrylic acid, based on the total weight of the acrylic acid fed via the second stream (2) to the reaction zone (RZ).

Such a pure acrylic acid may have, for example, the following composition:

acrylic acid 99.5 to 99.9% by weight, acetic acid 50 to 1500 ppm by weight, propionic acid 10 to 500 ppm by weight,

diacrylic acid 10 to 1000 ppm by weight, water 50 to 1000 ppm by weight, aldehydes 10 to 50 ppm by weight, other carbonyl-containing inhibitors 100 to 300 ppm by weight, and maleic acid (anhydride) 10 to 20 ppm by weight, wherein the values for the weight are in each case based on the total weight of the pure acrylic acid fed via the second stream (2) to the reaction zone (RZ).

Acidic Catalyst

In the inventive process in step i) the alcohol and (meth) acrylic acid are reacted in the reaction zone (RZ) to obtain a product mixture comprising the (meth)acrylate and unreacted (meth)acrylic acid and unreacted alcohol. The reaction of the alcohol and (meth)acrylic acid in the reaction zone (RZ) is preferably conducted in the presence of at least one acidic catalyst Suitable acidic catalysts are sulfuric acid, para-toluenesulfonic acid, benzenesulfonic acid, dodecylbenzenesulfonic acid, methanesulfonic acid or mixtures thereof, acidic ion exchangers also being possible.

Sulfuric acid, para-toluenesulfonic acid and methanesulfonic acid are preferably used, particularly preferred is sulfuric acid.

The catalyst concentration is, for example, from 0.1 to 5, preferably from 0, 5 to 3, % by weight, based on the reaction mixture in the reaction zone (RZ).

The catalyst is preferably fed to the reaction zone (RZ) via a sixth stream (6).

Reaction Zone (RZ)

The reaction zone (RZ) in which the alcohol and the (meth)acrylic acid are reacted to obtain the product mixture comprising the (meth)acrylate, unreacted (meth)acrylic acid and unreacted alcohol are known to the person skilled in the art.

In a preferred embodiment the reaction zone (RZ) comprises one to three reactors (R1, R2, R3). The reaction zone (RZ) may comprise a first reactor (R1), the reaction zone (RZ) may comprise a first reactor (R1) and a second reactor (R2) and the reaction zone (RZ) may comprise a first reactor (R1), a second reactor (R2) and a third reactor (R3), wherein in a preferred embodiment in each case on the top of the first reactor (R1) a distillation column (DC) is located.

The setpoint for the molar ratio of the (meth)acrylic acid and the alcohol in the total feed of the (meth)acrylic acid and the alcohol to the reaction zone (RZ) is preferably in the range of 1:0.9 to 1:1.25 more preferably in the range of 1:0.95 to 1:1.2 and most preferably in the range of 1:1 to 1:1.15.

Another object of the present invention, therefore is a process wherein the setpoint for the molar ratio of the (meth)acrylic acid and the alcohol in the total feed of the (meth)acrylic acid and the alcohol to the reaction zone (RZ) is in the range of 1:0.9 to 1:1.25.

The temperature in the first reactor (R1) of the reaction zone (RZ) is preferably in the range of 95 to 120° C. The temperature in the second reactor (R2) of the reaction zone (RZ) is preferably in the range of 105 to 125° C. In a preferred embodiment the temperature in the second reactor (R2) of the reaction zone (RZ) is higher than the temperature in the first reactor (R1).

In the reaction zone (RZ) the product mixture is obtained comprising the (meth)acrylate, unreacted (meth)acrylic acid and unreacted alcohol. In step ii) of the inventive process the product mixture is fed via a third stream (3) to a separation zone (SZ).

Product Mixture

The product mixture comprises the (meth)acrylate, unreacted (meth)acrylic acid and unreacted alcohol. The product mixture moreover may comprise water acidic catalyst and/or byproducts formed during the reaction. The product mixture comprises preferably 65 to 90% by weight of (meth)acrylate, 0.1 to 10% by weight of unreacted (meth)acrylic acid and 3 to 12% by weight of unreacted alcohol, 0 to 3% by weight of water and 1 to 20% by weight of byproducts, in each case based on the total weight of the product mixture.

Another object of the present invention, therefore is a process wherein the product mixture comprises preferably 65 to 90% by weight of (meth)acrylate, 0.1 to 10% by weight of unreacted (meth)acrylic acid and 3 to 12% by weight of unreacted alcohol, 0 to 3% by weight of water and 1 to 20% by weight of byproducts, in each case based on the total weight of the product mixture.

Sensor (S)

In step ii) of the inventive process the product mixture is fed via a third stream (3) to a separation zone (SZ) and the sensor (S) determines the molar ratio of the unreacted (meth)acrylic acid and the unreacted alcohol contained in the product mixture. Depending on the determined molar ratio of the unreacted (meth)acrylic acid and the unreacted alcohol in the product mixture the sensor (S) closed-loop controls the first control unit ($R_{AL}$) and/or the second control unit ($R_{AA}$).

The sensor (S) can, for example, be located in the reaction zone (RZ). The sensor (S) can, for example, also be located in or at the third stream (3). If the sensor (S) is located in the reaction zone (RZ) it can be located, if present, in the first reactor (R1), in the second reactor (R2), in the third reactor (R3) or between the first reactor (R1) and the second reactor (R2) or between the second reactor (R2) and the third reactor (R3).

In a preferred embodiment the sensor (S) is located in or at the third stream (3).

Another object of the present invention, therefore is a process wherein the sensor (S) determines the molar ratio of the unreacted (meth)acrylic acid and the unreacted alcohol in or at the third stream (3).

In a preferred embodiment the sensor (S) determines the molar ratio of the unreacted (meth)acrylic acid and the unreacted alcohol contained in the product mixture by NIR-spectroscopy. More preferred the sensor (S) determines the molar ratio of the unreacted (meth)acrylic acid and the unreacted alcohol in or at the third stream (3).

The term "in or at the third stream (3)" for the purpose of the present invention means that the sensor (S) is located inside of the third stream (3) or beside the third stream (3).

The determination of the molar ratio of the unreacted (meth)acrylic acid and the unreacted alcohol contained in the product mixture by the sensor (S) can be carried out offline, online or inline. The measurement (determination) is preferably carried out online or inline, particularly preferably online.

The sensor (S), hereinafter also denominated as measuring instrument (MI) thus preferably records an NIR spectrum of the product mixture online. For the purpose of the present invention the terms "sensor (S)" and "measuring instrument (MI)" are used synonymously and have the same meaning.

The present invention therefore also provides a process method in which the measuring instrument (MI) records the NIR spectrum of the product mixture online or inline.

Another object of the present invention, therefore is a process wherein the sensor (S), controls the first control unit ($R_{AL}$) and/or the second control unit ($R_{AA}$) online or inline.

For the purposes of the present invention, "offline" means that a sample of the product mixture is taken manually and optionally treated. The measurement is subsequently carried out by means of the measuring instrument (MI) and the molar ratio of the unreacted (meth)acrylic acid and the unreacted alcohol contained in the product mixture is determined by evaluation of the results of the measurement using the measuring instrument (MI). An offline measurement is carried out discontinuously.

"Online" means that the product mixture is measured continuously by means of the measuring instrument (MI). The third stream (3) then usually comprises a measuring instrument (MI). The measurement is carried out via a bypass tube through which the part of the product mixture to be measured is conveyed. Manual sampling is dispensed with, in contrast to offline measurement, but it is necessary to pass part of the product mixture through a bypass tube.

For the present purposes, "inline" means that the product mixture is measured continuously and that the measurement takes place directly in the third stream (3) stream. Passage of the product mixture through a bypass tube is thus dispensed with.

Methods of carrying out offline, inline and online measurements are known per se to those skilled in the art.

The position of the measuring instrument (MI) is dependent on whether the measurement is carried out offline, online or inline.

The determination of the molar ratio of the unreacted (meth)acrylic acid and the unreacted alcohol contained in the product mixture is preferably carried out NIR-spectroscopically. For the purposes of the present invention, "NIR-spectroscopically" means that a measuring instrument (MI) measures an NIR spectrum (near infrared spectrum). As measuring instrument (MI), use is usually made of an NIR spectrometer. NIR spectrometers are known per se to those skilled in the art.

As NIR spectrometer, preference is given to a FT-NIR spectrometer (Fourier transform near-infrared spectrometer) which measures in transmission.

Another object of the present invention, therefore is a process wherein for the NIR-spectroscopy a Fourier transform near-infrared spectrometer which measures in transmission is used.

Such spectrometers are known to those skilled in the art.

The measuring instrument (MI) measures, for example, a NIR spectrum in the range from 12 500 to 4000 $cm^{-1}$, preferably in the range from 10 000 to 5000 $cm^{-1}$ and particularly preferably in the range from 7000 to 5400 $cm^{-1}$.

The present invention therefore also provides a process in which the NIR spectrum recorded by the measuring instrument (MI) is in the range from 12 500 to 4000 $cm^{-1}$.

The NIR spectrum measured by means of the measuring instrument (MI) is then evaluated, for example, by means of a chemometric calibration model, preferably a partial least squares method (PLS method), and the concentrations in the product mixture are determined. Methods for this are known per se to those skilled in the art and are described, for example, in Jörg-Peter Conzen "*Multivariate Kalibration*", 2001, ISBN 3-929431-13-0, in Richard Kramer "*Chemometric Techniques for Quantitative Analysis*", 1998, ISBN 0-8247-0198-4 and in C. Miller "*Chemometrics for online spectroscopy applications—theory and practice*". Journal of chemometrics 2000. 14. The evaluation is carried out, for example, in the range from 12 500 to 4000 $cm^{-1}$, preferably in the range from 9500 to 5000 $cm^{-1}$, particularly preferably in the range from 9400 to 5400 $cm^{-1}$ and in particular in the range from 6100 to 5550 $cm^{-1}$.

In a preferred embodiment of the inventive process the setpoint for the molar ratio of the unreacted (meth)acrylic acid and the unreacted alcohol in the product mixture is in the range of 1:0.5 to 1:10 more preferably in the range of 1:0.75 to 1:2 and most preferably in the range of 1:0.8 to 1:1.2 wherein the sensor (S), when determining leaving the setpoint range of the molar ratio in the product mixture, controls the first control unit ($R_{AL}$) and/or the second control unit ($R_{AA}$).

Another object of the present invention, therefore is a process wherein the setpoint for the molar ratio of the unreacted (meth)acrylic acid and the unreacted alcohol in the product mixture is in the range of 1:0.5 to 1:10 and, wherein the sensor (S), when determining leaving the setpoint range of the molar ratio in the product mixture, controls the first control unit ($R_{AL}$) and/or the second control unit ($R_{AA}$).

The sensor (S) closed-loop controls the first control unit ($R_{AL}$) and/or the second control unit ($R_{AA}$) in such a way that the set point range of the molar ratio of (meth)acrylic acid and the alcohol in the total feed of (meth)acrylic acid and alcohol to the reaction zone (RZ), as mentioned above.

The first control unit ($R_{AL}$) may be any device which is capable to control the feed of the alcohol to the reaction zone (RZ) via the first stream (1). Suitable devices that may be used as first control unit ($R_{AL}$) are for example valves or pumps.

The second control unit ($R_{AA}$) may be also any device which is capable to control the feed of the (meth)acrylic acid to the reaction zone (RZ) via the second stream (2). Suitable devices that may be used as second control unit ($R_{AA}$) are for example valves or pumps.

"Control" and "closed-loop control" are known per se to those skilled in the art. Closed-loop control is also denominated as "regulation".

In the case of control, an input variable influences an output variable. However, in the case of control, the output variable does not have an effect back on the input variable. The input variable is thus not influenced by the output variable. An open regulating circuit is thus present.

In contrast thereto. in the case of closed-loop control (regulation) as used in the When the value to be regulated deviates from the set value, a manipulated variable is appropriately adapted. A measured input variable therefore influences an output variable and the output variable has an effect back on the input variable. A closed regulating circuit is thus present.

Another object of the present invention is a process wherein the molar amount per hour of alcohol fed to the reaction zone (RZ) via the first stream (1) is set to a fixed value and the molar ratio of the (meth)acrylic acid and the alcohol in the total feed of the (meth)acrylic acid and the alcohol to the reaction zone (RZ) is adjusted by the second control unit ($R_{AA}$) which is closed-loop controlled by the sensor (S).

Another object of the present invention is a process wherein the molar amount per hour of (meth)acrylic acid fed to the reaction zone (RZ) via the second stream (2) is set to a fixed value and the molar ratio of the (meth)acrylic acid and the alcohol in the total feed of the (meth)acrylic acid and the alcohol to the reaction zone (RZ) is adjusted by the first control unit ($R_{AL}$) which is closed-loop controlled by the sensor (S).

Separation Zone (SZ)

The product mixture is fed via the third stream (3) to a separation zone (SZ). According to step iii) of the inventive process in the separation zone (SZ) the product mixture is separated to obtain the (meth)acrylate and a recycling mixture comprising the unreacted (meth)acrylic acid and the unreacted alcohol. The (meth)acrylate is discharged from the separation zone (SZ) as fourth stream (4) the recycling mixture is discharged from the separation zone (SZ) as fifth stream (5). The separation zone (SZ) may comprise any device or apparatus which is suitable to separate the product mixture in order to obtain the (meth)acrylate and the recycling mixture. Suitable devices for the separation zone are for example distillation columns, extraction columns and/or extraction vessels.

In a preferred embodiment the recycling mixture is recycled to the reaction zone via fifth stream (5).

Another object of the present invention, therefore is a process wherein the fifth stream (5) discharged from the separation zone (SZ) is recycled to the reaction zone (RZ).

In one embodiment of the present invention the recycling mixture is directly recycled from the separation zone (SZ) to the reaction zone (RZ). In a preferred embodiment the recycling mixture is further worked up in order to remove byproducts, like Michael adducts and subsequently recycled to the reaction zone (RZ)

The work up of the recycling mixture may be carried up in any work up device (WU) which is capable to separate off byproducts form the recycling mixture. Form the work up device (WU) the worked up recycling mixture may be fed via the worked up fifth stream (5a) to the reaction zone (RZ).

The workup process of the recycling mixture can comprise one or more workup steps. The workup steps can be carried out continuously batch wise. By consequence in one embodiment of the inventive process the molar ratio of the unreacted (meth)acrylic acid and the unreacted alcohol contained in the fifth stream (5) and/or the amount of the unreacted (meth)acrylic acid and the unreacted alcohol contained in the fifth stream (5) changes with time.

Another object of the present invention, therefore is a process wherein the molar ratio of the unreacted (meth) acrylic acid and the unreacted alcohol contained in fifth stream (5) and/or the unreacted (meth)acrylic acid and the unreacted alcohol contained in the fifth stream (5) changes with time.

The fifth stream (5) or the worked up fifth stream (5a) may be fed to the reaction zone (RZ) as a separate feed. It is also possible to feed the fifth stream (5) or the worked up fifth stream (5a) to the first stream (1) and/or to the second stream (2). Preferably the fifth stream (5) or the worked up fifth stream (5a) is fed to the second stream (2) preferably behind (downstream) the second control unit ($R_{AA}$).

Another object of the present invention is the use of a sensor (S) which measures, a NIR spectrum in the range from 12 500 to 4000 $cm^{-1}$, preferably in the range from 10 000 to 5000 $cm^{-1}$ and particularly preferably in the range from 7000 to 5400 $cm^{-1}$ in a process for the continuous preparation of a (meth)acrylate by reacting an alcohol with (meth)acrylic acid for the regulation of the molar ratio of (meth)acrylic acid and alcohol in the total feed of the (meth)acrylic acid and the alcohol to a reaction zone (RZ), wherein in the reaction zone (RZ) (meth)acrylic acid and alcohol are reacted to obtain (meth)acrylate.

LIST OF REFERENCE SIGNS $R_{AL}$ first control unit which can be closed-loop controlled by sensor S
$R_{AA}$ second control unit which can be closed-loop controlled by sensor S
RZ reaction zone R1 first reactor of the reaction zone RZ
R2 second reactor of the reaction zone RZ
DC distillation column of the reaction zone RZ
WU work up device
S sensor
1 first stream containing the alcohol
2 second stream containing the (meth)acrylic acid
3 third stream comprising the (meth)acrylate, unreacted (meth)acrylic acid and unreacted alcohol; product mixture
4 fourth stream comprising (meth)acrylate
5 fifth stream comprising unreacted (meth)acrylic acid and unreacted alcohol; recycling mixture
5a worked up fifth stream
6 sixth stream containing the acidic catalyst In the embodiment according to FIG. 1, a first stream 1 containing the alcohol is fed to the reaction zone RZ and a second stream 2 containing the (meth)acrylic acid is fed to the reaction zone RZ. The amount of alcohol fed to the reaction zone RZ via the first stream 1 can be adjusted by a first control unit $R_{AL}$ and the amount of (meth)acrylic acid, which is fed via stream 2 to the reaction zone RZ can be adjusted by a second control unit $R_{AA}$. In the reaction zone, the alcohol and the (meth)acrylic acid are reacted and a product mixture comprising the (meth)acrylate and unreacted (meth)acrylic acid and unreacted alcohol is obtained. The product mixture is fed via a third stream 3 to a separation zone. The molar ratio of unreacted (meth)acrylic acid and alcohol can be measured by a sensor S. In the separation zone SZ, the production mixture is separated to obtain the (meth)acrylate which is discharged from the separation zone SZ, as fourth stream 4, and a recycling mixture comprising the unreacted (meth)acrylic acid and the unreacted alcohol which is discharged from the separation zone SZ as a fifth stream 5. The fifth stream 5 is recycled to the reaction zone RZ.

Figure 2:
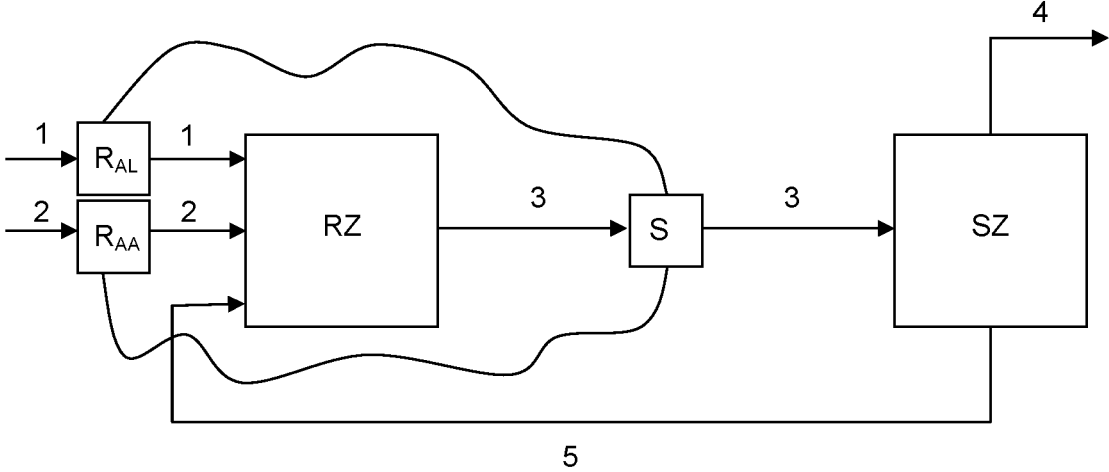
FIG. 2 is a flow diagram for another process in accordance with the present disclosure wherein the first control unit and/or second control unit are closed-loop controlled.
Figure 3:
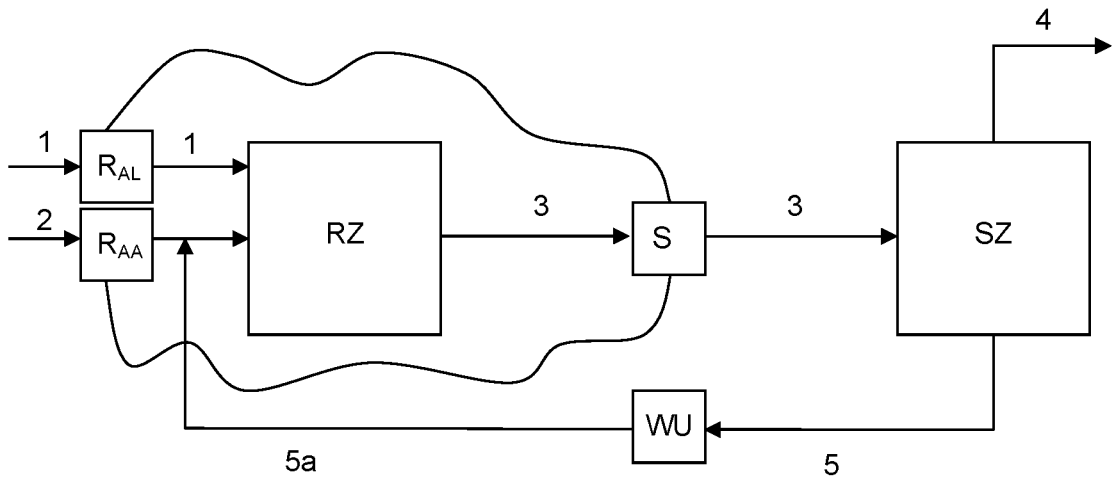
FIG. 3 is a flow diagram for another process in accordance with the present disclosure wherein the recycling mixture is further worked up.

FIG. 2 shows an embodiment wherein the first control unit $R_{AL}$ and/or the second control unit $R_{AA}$ is/are closed-loop controlled by the sensor S. FIG. 3 shows an embodiment similar to FIG. 2, wherein the recycling mixture (fifth stream 5) is further worked up in a work-up device WU to obtain a worked-up fifth stream 5a which is fed to the reaction zone RZ by admixing the worked-up fifth stream 5a with the second stream 2 behind (downstream) the second control unit $R_{AA}$.

Figure 4:
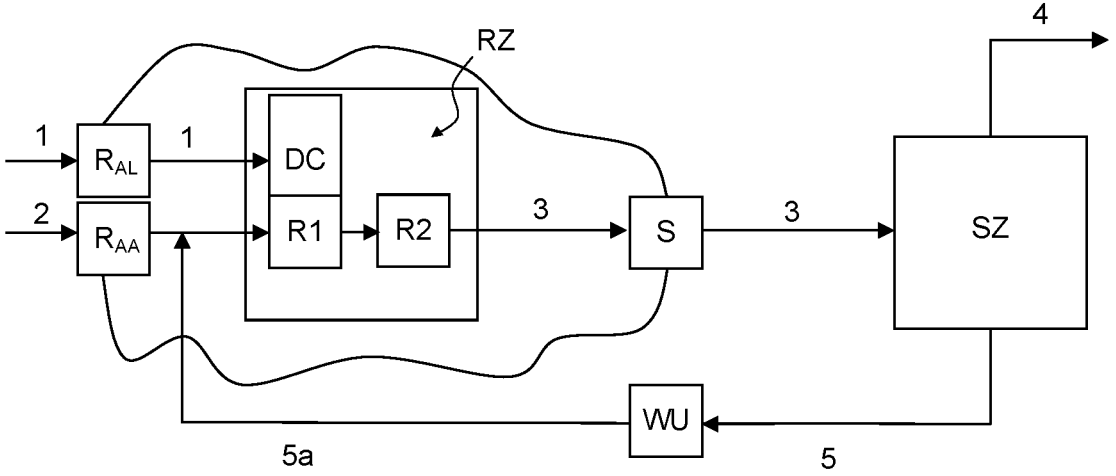
FIG. 4 is a flow diagram for another process in accordance with the present disclosure wherein there is a distillation column on top of the first reactor.

FIG. 4 shows an embodiment of the invention similar to FIG. 3, wherein the reaction zone RZ comprises a first reactor R1 and a second reactor R2, wherein on top of the first reactor R1 a distillation column DC is located. The first stream 1 is fed in the distillation column of the reaction zone RZ and the second stream 2 is fed to the first reactor R1 of the reaction zone RZ.

The invention claimed is:

1. A process for the continuous preparation of a (meth) acrylate by reacting an alcohol with (meth)acrylic acid comprising the steps:

i) feeding a first stream containing the alcohol and a second stream containing the (meth)acrylic acid to a reaction zone (RZ), wherein the feed to the reaction zone (RZ) via the first stream is adjusted by a first control unit ($R_{AA}$) which is closed-loop controlled by a sensor (S) and/or the feed to the reaction zone (RZ) via the second stream is adjusted by a second control unit ($R_{AA}$) which is closed-loop controlled by the sensor (S), and reacting the alcohol and the (meth)acrylic acid in the reaction zone (RZ) to obtain a product mixture comprising the (meth)acrylate and unreacted (meth) acrylic acid and unreacted alcohol, ii) feeding the product mixture as a third stream from the reaction zone (RZ) to a separation zone (SZ), wherein the sensor (S) determines a molar ratio of the unreacted (meth)acrylic acid and the unreacted alcohol contained in the product mixture and, wherein the sensor (S), depending on the determined molar ratio of the unreacted (meth)acrylic acid and the unreacted alcohol in the product mixture, controls the first control unit ($R_{AL}$) and/or the second control unit ($R_{AA}$), and iii) separating the product mixture in the separation zone (SZ) to obtain the (meth)acrylate which is discharged from the separation zone (SZ) as a fourth stream and a recycling mixture comprising the unreacted (meth) acrylic acid and the unreacted alcohol which is discharged from the separation zone (SZ) as a fifth stream.

2. The process according to claim 1, wherein the sensor (S) determines the molar ratio of the unreacted (meth)acrylic acid and the unreacted alcohol contained in the product mixture by NIR-spectroscopy.

3. The process according to claim 1, wherein the fifth stream discharged from the separation zone (SZ) is recycled to the reaction zone (RZ).

4. The process according to claim 1, wherein the setpoint for the molar ratio of the (meth)acrylic acid and the alcohol in a total feed of the (meth)acrylic acid and the alcohol to the reaction zone (RZ) is in the range of 1:0.9 to 1:1.25.

5. The process according to claim 1, wherein the molar ratio of the unreacted (meth)acrylic acid and the unreacted alcohol contained in the fifth stream and/or the amount of the unreacted (meth)acrylic acid and the unreacted alcohol contained in the fifth stream changes with time.

6. The process according to claim 1, wherein the setpoint for the molar ratio of the unreacted (meth)acrylic acid and the unreacted alcohol in the product mixture is in the range of 1:0.5 to 1:10 and, wherein the sensor (S), when determining leaving the setpoint range of the molar ratio in the product mixture, controls the first control unit ($R_{AL}$) and/or the second control unit ($R_{AA}$).

7. The process according to claim 6, wherein the sensor (S), controls the first control unit ($R_{AL}$) and/or the second control unit ($R_{AA}$) online or inline.

8. The process according to claim 1, wherein molar amount per hour of alcohol fed to the reaction zone (RZ) via the first stream is set to a fixed value and the molar ratio of the (meth)acrylic acid and the alcohol in a total feed of the (meth)acrylic acid and the alcohol to the reaction zone (RZ) is adjusted by the second control unit ($R_{AA}$) which is closed-loop controlled by the sensor (S).

9. The process according to claim 1, wherein molar amount per hour of (meth)acrylic acid fed to the reaction zone (RZ) via the second stream is set to a fixed value and the molar ratio of the (meth)acrylic acid and the alcohol in a total feed of the (meth)acrylic acid and the alcohol to the reaction zone (RZ) is adjusted by the first control unit ($R_{AL}$) which is closed-loop controlled by the sensor (S).

10. The process according to claim 1, wherein the sensor (S) determines the molar ratio of the unreacted (meth)acrylic acid and the unreacted alcohol in or at the third stream.

11. The process according to claim 1, wherein the product mixture comprises 65 to 90% by weight of (meth)acrylate, 0.1 to 10% by weight of unreacted (meth)acrylic acid and 3 to 12% by weight of unreacted alcohol, 0 to 3% by weight of water and 1 to 20% by weight of byproducts, in each case based on a total weight of the product mixture.

12. The process according to claim 1, wherein for the NIR-spectroscopy a Fourier transform near-infrared spectrometer which measures in transmission is used.

13. The process according to claim 1, wherein the sensor (S) measures, a NIR spectrum in the range from 12,500 to 4000 cm$^{-1}$.

14. A process for continuous preparation of a (meth) acrylate by reacting an alcohol with (meth)acrylic acid comprising measuring an NIR spectrum in the range from 12,500 to 4000 cm$^{-1}$ with a sensor for regulation of a molar ratio of (meth)acrylic acid and alcohol in a total feed of the (meth)acrylic acid and the alcohol to a reaction zone (RZ) and wherein in the reaction zone (RZ) (meth)acrylic acid and alcohol are reacted to obtain (meth)acrylate.

\* \* \* \* \*